United States Patent
Liu et al.

(10) Patent No.: US 10,807,893 B2
(45) Date of Patent: *Oct. 20, 2020

(54) POLYHYDROXYALKANOATE PRODUCTION DURING WASTEWATER TREATMENT

(71) Applicants: Hsinying Liu, Sacramento, CA (US); Michael Wayne Falk, Jr., Sacramento, CA (US)

(72) Inventors: Hsinying Liu, Sacramento, CA (US); Michael Wayne Falk, Jr., Sacramento, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 15/966,978

(22) Filed: Apr. 30, 2018

(65) Prior Publication Data

US 2018/0273407 A1 Sep. 27, 2018

Related U.S. Application Data

(63) Continuation-in-part of application No. 14/875,337, filed on Oct. 5, 2015, now abandoned, which is a continuation of application No. 13/206,327, filed on Aug. 9, 2011, now Pat. No. 9,150,445.

(51) Int. Cl.
*C02F 3/12* (2006.01)
*C12P 7/42* (2006.01)
*C12P 7/62* (2006.01)
*C02F 3/34* (2006.01)

(52) U.S. Cl.
CPC ............ *C02F 3/12* (2013.01); *C12P 7/42* (2013.01); *C12P 7/625* (2013.01); *C02F 3/1221* (2013.01); *C02F 3/1263* (2013.01); *C02F 3/34* (2013.01); *C02F 2209/001* (2013.01); *C02F 2209/10* (2013.01); *Y02W 10/15* (2015.05); *Y02W 10/45* (2015.05)

(58) Field of Classification Search
CPC ........ C02F 3/12; C02F 3/1221; C02F 3/1263; C02F 3/34; C02F 2209/001; C02F 2209/10; C12P 7/42; C12P 7/625; Y02W 10/15; Y02W 10/45
See application file for complete search history.

(56) References Cited

U.S. PATENT DOCUMENTS

| | | | |
|---|---|---|---|
| 5,240,597 A | 8/1993 | Ueda |
| 5,324,563 A | 6/1994 | Rogers et al. |
| 6,737,263 B2 | 5/2004 | Dragotta et al. |
| 6,987,011 B1 | 1/2006 | Reid et al. |
| 6,991,931 B2 | 1/2006 | Dragotta et al. |
| 7,267,974 B2 | 9/2007 | Kozaki et al. |
| 7,435,566 B2 | 10/2008 | Ogawa et al. |
| 7,514,525 B2 | 4/2009 | Yu |
| 7,579,176 B2 | 8/2009 | Herrema et al. |
| 7,887,893 B2 | 2/2011 | Billington et al. |
| 2002/0031812 A1 | 3/2002 | Lapointe et al. |
| 2002/0052016 A1 | 5/2002 | Dragotta et al. |
| 2004/0152151 A1 | 8/2004 | Dragotta et al. |
| 2007/0202581 A1 | 8/2007 | Herrema et al. |
| 2008/0203015 A1 | 8/2008 | Marston et al. |
| 2009/0317879 A1 | 12/2009 | Criddle et al. |
| 2010/0035313 A1 | 2/2010 | Satou et al. |
| 2010/0078389 A1 | 4/2010 | Elektorowicz et al. |
| 2010/0190221 A1 | 7/2010 | Herrema et al. |
| 2010/0200498 A1 | 8/2010 | Bengtsson et al. |
| 2010/0255540 A2 | 10/2010 | Herrema et al. |
| 2011/0104767 A1 | 5/2011 | Kawata et al. |

FOREIGN PATENT DOCUMENTS

| | | |
|---|---|---|
| WO | 2011070544 A2 | 6/2011 |
| WO | 2011073744 A1 | 6/2011 |

OTHER PUBLICATIONS

Dutta, A., et al. 2015 Curr Pollution Rep 1: 177-190. (Year: 2015).*
Liu, Hsin-Ying, et al., Production of Polyhydroxyalkanoate During Treatment of Tomato Cannery Wastewater, Water Environment Research, vol. 80, No. 4, Apr. 2008.
Liu, Hsin-Ying, et al., Factorial Experimental Designs for Enhancement of Concurrent Ply(Hydroxyalkanoale) Production and Brewery Wastewater Treatment, Water Environment Research, vol. 83, No. 1, Jan. 2011.
Dionisi, Davide, et al., Biodegradable Polymers From Organic Acids by Using Activated Sludge Enriched by Aerobic Periodic Feeding, Biotechnology and Bioengineering, vol. 85, No. 6 Mar. 20, 2004.
Coats, Erik R., et al., Toward Polyhydroxyalkanoate Production Concurrent with Municipal Wastewater Treatment in a Sequencing Batch Reactor System, Journal of Environmental Engineering, pp. 46-54, Jan. 2011.

(Continued)

*Primary Examiner* — Marsha Tsay
(74) *Attorney, Agent, or Firm* — Shook, Hardy & Bacon LLP

(57) ABSTRACT

A wastewater treatment process elicits microorganisms to convert a waste stream/organic resource to intracellular biopolymer polyhydroxyalkanoate (PHA). The process includes (i) waste stream/organic resource composition feed criteria, (ii) configuration coupled with operational parameters, and (iii) PHA-laden biomass separation and stabilization. A waste stream/organic resource capable of producing enhanced levels of PHA may be selected based on a combination of criteria, which may include short chain fatty acid concentration, protein concentration, polysaccharides concentration, and total suspended solids concentration. The waste stream is introduced into an aeration basin or sequencing batch reactor upon a specific configuration and operated under various parameter combinations for selecting/enriching microorganisms capable of producing PHA. The PHA-laden biomass is separated and stabilized for downstream PHA related product beneficial uses. The present process achieves concurrent wastewater treatment and PHA production, where PHA level (of more than 10% on a cell-weight basis) otherwise could not be obtained.

20 Claims, 4 Drawing Sheets

(56) References Cited

OTHER PUBLICATIONS

Takabatake, H., et al., Recovery of biodegradable plastics from activated sludge process, Water Science and activated sludge process, Water Science and Technology, vol. 42 Nos. 3-4, pgs. 351-356, IWA Publishing 2000.
Chiellini et al. (2001), Biorelated Polymers: Sustainable Polymer Science and Technology, Kluwer Academic/Plenum Publishers, New York, p. 134.
Coats et al., Functional Stability of a Mixed Microbial Consortium Producing PHA From Waste Carbon Sources, Applied Biochemistry and Biotechnology (2007), vol. 136-140, pp. 909-925.
Liu Ph.D. dissertation (2009) Bioplastics Poly(hydroxyalkanoate) Production during Industrial Wastewater Treatment.
Bengtsson, S., et al. 2008 Bioresource Technology 99: 509-516. (Year:2008).
Chakravarty, P., et al. 2010 Bioresource Technology 101: 2896-2899. (Year: 2010).

* cited by examiner

POLYHYDROXYALKANOATE PRODUCTION DURING WASTEWATER TREATMENT

RELATED APPLICATION

This patent application is a continuation-in-part of U.S. application Ser. No. 14/875,337, filed Oct. 5, 2015, which is a continuation of U.S. application Ser. No. 13/206,327, filed Aug. 9, 2011, both of which are incorporated herein by reference in their entireties.

BACKGROUND

Polyhydroxyalkanoates (PHAs) are biologically derived polymers (or bioplastic) synthesized as intracellular storage materials by microorganisms metabolizing renewable organic carbon sources. The physical properties of PHA polymers are similar to those of conventional plastics (such as polypropylene (PP) and polyethylene (PE)). In contrast with traditional petroleum-based plastics, biomass-derived PHAs are generated from renewable carbon resources and are 100% biodegradable following disposal. Experts within the field consider PHAs as a potential "green" substitute to conventional plastics.

SUMMARY

Embodiments of the invention are defined by the claims below, not this summary. A high-level overview of various aspects of the invention are provided here for that reason, to provide an overview of the disclosure, and to introduce a selection of concepts that are further described in the detailed description section below. This summary is not intended to identify key features or essential features of the claimed subject matter, nor is it intended to be used as an aid in isolation to determine the scope of the claimed subject matter.

Embodiments of the present invention relate to enhanced polyhydroxyalkanoates (PHAs) production during wastewater treatment. A waste stream/organic resource that is suitable for increased PHA production may initially be identified based on a combination of constituents criteria. The criteria may include total suspended solids, short chain fatty acids concentration, protein concentration, and polysaccharides concentration. In some embodiments, the waste stream/organic resource may optionally be pre-treated to provide the constituents criteria. The waste stream/organic resource is introduced into an aeration basin or sequencing batch reactor (SBR) that may be operated under conditions for selecting and enhancing microorganisms capable of accumulating PHA. PHA-laden biomass is separated and stabilized for beneficial PHA use.

BRIEF DESCRIPTION OF THE DRAWINGS

Embodiments of the present invention are described in detail below with reference to the attached drawing figures, and wherein.

DETAILED DESCRIPTION

Figure 1:
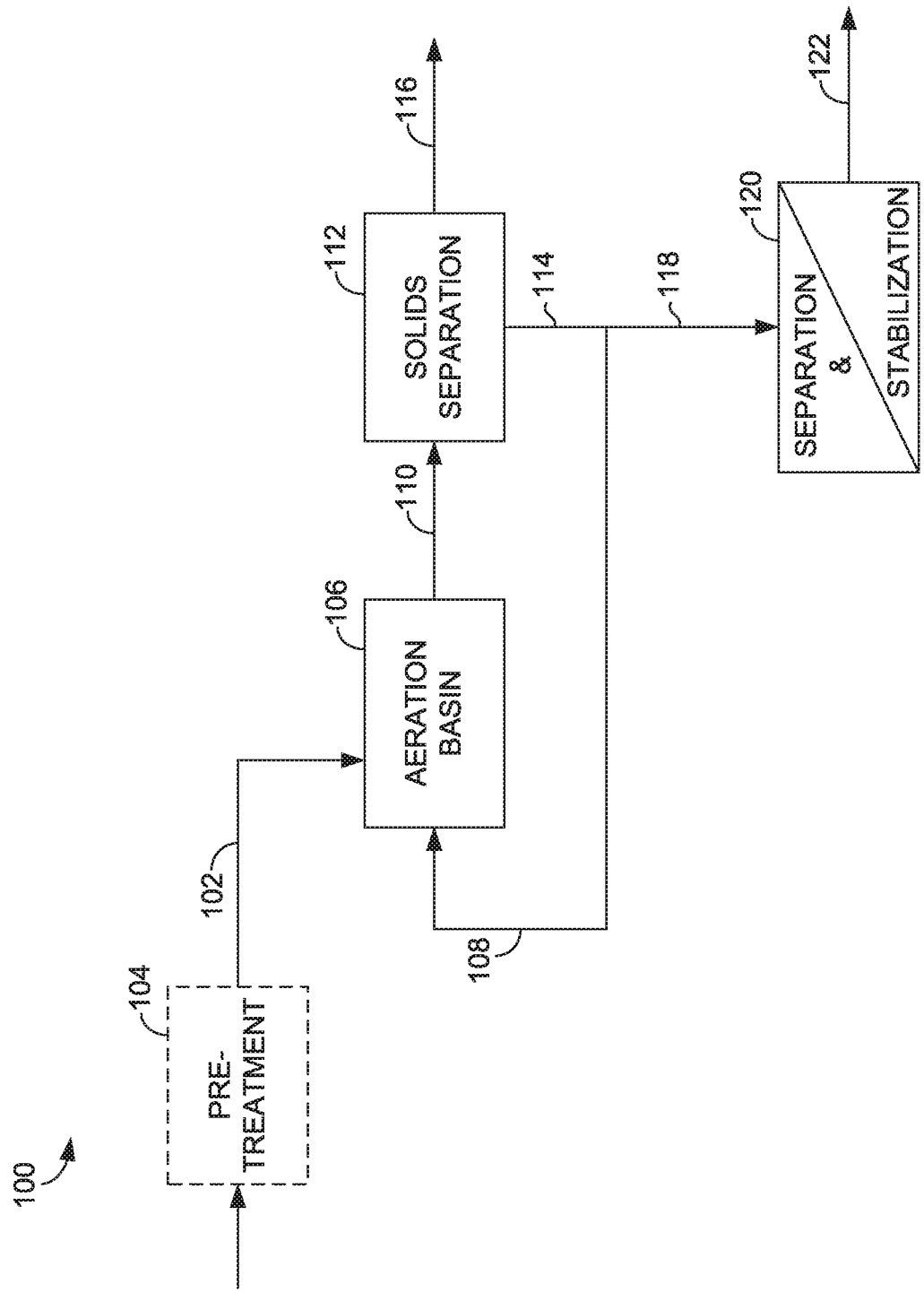
FIG. 1 illustrates a schematic diagram of PHA production during waste stream reclamation/organic resource recovery in accordance with an embodiment of the present invention.

The subject matter of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" may be used herein to connote different elements of methods employed, the terms should not be interpreted as implying any particular order among or between various steps herein disclosed unless and except when the order of individual steps is explicitly described.

Embodiments of the present invention are generally directed to producing increased polyhydroxyalkanoates (PHAs) during treatment of wastewater by converting the organic matter in the wastewater into intracellular PHA during an activated sludge (AS) process. Accordingly, the process achieves simultaneous wastewater treatment performance and increased PHA production within a bioreactor. In conventional/regular wastewater treatment process, the PHA in AS is typically less than 2.5% on a cell-weight basis. In contrast, embodiments of the present invention may produce AS with PHA above 10% on a cell-weight basis.

While conventional AS processes are designed based on biological growth physiology in which environmental conditions are provided for microorganisms to convert organics in wastewater to biomass growth, embodiments of the present invention provide a process that is based on a storage-oriented perspective. Generally, environmental conditions govern the fate and conversion of organic matter by microbial consortia as either storage (i.e., PHA or glycogen accumulation) or growth response (i.e., biomass assimilation). Embodiments of the present invention focus on recovering the organic carbon by storage as the intracellular biopolymer, PHA. This is provided by selecting a waste stream with particular constituent characteristics and employing operational criteria that foster PHA storage-oriented AS (instead of growth-oriented AS as in traditional wastewater treatment). Subsequently, the excess AS that is commonly wasted in a traditional WWTP can be collected and treated for the downstream beneficial use as the AS contains a substantially higher amount of PHA.

In accordance with embodiments of the present invention, a waste stream that is suitable for enhanced PHA production is initially selected. In particular, this may include evaluating the constituents of existing waste streams to identify a rapidly biodegradable, high carbon-content waste stream having PHA precursor metabolites such that the waste stream promotes a rapid mass transport of the substrate within microbial cells, which subsequently triggers the microbial storage-response metabolism. The constituents of a waste steam evaluated may include the short chain fatty acids (SCFAs) concentration, the polysaccharides concentration, and the protein concentration.

SCFAs are primary precursor metabolites for PHA production. Accordingly, the waste stream should have a minimum level of SCFAs to promote PHA production. In some embodiments, a waste stream with a SCFAs concentration greater than 1 mM is preferred.

Polysaccharides and protein each provide competition with (and therefore interfere with) the production of PHA. In particular, given that polysaccharides and protein are two main cell components, a relatively high polysaccharide and protein content favors assimilation into microbial biomass and, therefore, fewer PHA storage polymers. The environmental conditions provided in the main reactor enrich microbial storage capacity. However, high polysaccharide content waste streams may result in the storage of glycogen (i.e., a type of polysaccharides) instead of PHAs. In some embodiments of the present invention, a waste stream having a polysaccharides concentration less than 6 mM and a protein concentration less than 1 mM is preferred.

The waste stream may further be evaluated for compounds toxic to bacteria. Preferably, the waste stream includes little to no toxic compounds to provide a non-toxic environment for microbes to survive and generate PHA.

In some embodiments, a waste stream may be selected with constituents that do not have a satisfactory SCFAs concentration, polysaccharides concentration, and/or protein concentration. In such embodiments, a pre-treatment process, such as fermentation of solids, may be employed to provide a pre-treated waste stream that meets the constituent criteria discussed above.

Solids may also interfere with reactor operation and "dilute" PHA content in the end products (i.e., PHA-laden biomass) while harvesting. Accordingly, in some embodiments, a waste stream is selected with minimum solids interference. Preferably, the waste stream has a total suspended solids (TSS) concentration less than 200 mg/L. If a waste stream is selected that has an undesirable level of solids (e.g., a TSS concentration more than 200 mg/L), a pre-treatment process that includes a solids separation step (e.g., clarification or filtration) may be employed to produce a pre-treated waste stream with reduced solids to minimize solids interference with PHA production.

With reference now to FIG. 1, a schematic view is provided that illustrates a wastewater treatment process 100 that provides concurrent PHA production in accordance with an embodiment of the present invention. As shown in FIG. 1, an influent waste stream 102 is treated in a manner to encourage PHA production during the treatment process. In some embodiments, the influent waste stream 102 is an untreated waste stream that includes the constituent characteristics (e.g., satisfactory SCFAs concentration, polysaccharides concentration, protein concentration, and suspended solids concentration) as described hereinabove. However, in other embodiments, one or more pre-treatment processes 104 may optionally be provided to produce the influent waste stream 102. The pre-treatment processes may include fermentation or other process to provide a satisfactory SCFAs concentration, polysaccharides concentration, and/or protein concentration. Additionally or alternatively, the pre-treatment processes 104 may include a solids removal process, such as clarification or filtration, to reduce the suspended solids concentration of the influent waste stream 102.

The influent waste stream 102 is introduced into an aeration basin 106 and mixed with return activated sludge (RAS) 108. In some embodiments, the aeration basin 106 may be operated as a plug-flow reactor. Additionally, the aeration basin 106 is configured with operational parameters that provide sufficient reaction time and a food to microorganism (F/M) ratio for microorganisms to uptake and deplete the substrate. The configuration ensures a famine-feast regime to select and enrich microbes capable of producing PHA. Under a feast-famine dynamic feeding pattern, AS is subjected to successive periods of external substrate availability (i.e., feast stage) and unavailability (i.e., famine stage), which generates a selective pressure that ensures microorganisms capable of generating internal storage reserves have a strong competitive advantage over those without the storage capacity. In particular, during the feast stage, microorganisms uptake available external substrate and convert it into intracellular PHA. Subsequently, PHA accumulating microorganisms consume PHA as an internal carbon source for survival during famine stage (i.e., external substrate unavailability). With respect to substrate availability, a conventional growth-oriented wastewater treatment process provides a feast stage until the external substrate is depleted; after which, treated effluent is ready to discharge. As such, in accordance with embodiments of the present invention, the location at which the influent waste stream 102 is introduced (as described in further detail below) coupled with the operational parameters of the aeration basin 106 provide a famine-feast regime (i.e., an additional famine region in front of the feast region).

The operational parameters used to provide the famine-feast regime to promote PHA production in some particular embodiments may include influent COD loading rate, hydraulic retention time (HRT), and F/M ratio. Generally, the influent COD loading rate may be higher than a conventional AS process. In some embodiments, the influent COD loading rate is between 800 mg/L/day and 3,500 mg/L/day. The F/M ratio may be higher than a conventional AS process; preferably, the F/M ratio is between 0.8 and 3.

The HRT may be higher than a conventional AS process. In some embodiments, longer HRTs, such as 2 or more days, may be employed to further promote the famine-feast regime. However, in other embodiments, the HRT may be as low as 1.5 days. To achieve a lower HRT (i.e., 1.5 days), the process reactor can initially be operated at a higher HRT (e.g., 2 or more days) to provide an environment that optimizes selecting/enriching microorganism capable of producing PHA. Those microorganisms may then be used to seed a process reactor with lower HRTs (e.g., 1.5 days).

As shown in FIG. 1, the RAS 108 is introduced substantially at the beginning of the aeration basin 106, while the influent waste stream 102 is introduced further down the aeration basin 106. In some embodiments, the influent waste stream 102 is introduced at a location that ranges from approximately ¼ to ¾ along the length of the aeration basin 106. Introducing the RAS 108 at the beginning of the aeration basin 106 while introducing the influent waste stream 102 further down the aeration basin 106 in this manner promotes the famine-feast regime that provides an environment that favors microorganisms capable of accumulating PHA. Therefore, an additional famine region in front of feast region promotes the enrichment/selection of PHA accumulating microorganisms. Additionally, maximum PHA production occurs at the end of the aeration basin 106/wastewater treatment (i.e. end of feast stage) as it is ready to be collected for downstream beneficial use. Meanwhile, the treated effluent is ready to discharge (since the external substrate is depleted at the end of the feast stage).

A treated waste stream 110 exiting the aeration basin 106 is processed in a solids separation basin 112, such as a clarifier, to separate AS 114 from an effluent 116. A first portion of the AS 108 is returned to the aeration basin 106 as the RAS 108. A second portion of the AS 118 is provided as a PHA-laden biomass to a separation and stabilization process 120. The separation and stabilization process 120 prevents microbes from consuming PHA as an internal carbon source following harvest and thereby produces a stabilized PHA-laden biomass 122. In some embodiments, the separation and stabilization process 120 may include dewatering (e.g., centrifugation) followed by microbial inactivation (e.g., disinfection) and an ensuing drying process.

Although only a single aeration basin 106, solids separation basin 112, and separation and stabilization process 120 are shown in FIG. 1, it should be understood that multiple aeration basins, solid separation basins, and separation and stabilization processes may be operated in parallel in accordance with embodiments of the present invention. Additionally, further basins and processes (such as a sequencing batch reactor (SBR)) not shown in FIG. 1 may be employed. Any and all such variations are contemplated to be within the scope of embodiments of the present invention.

Figure 2:
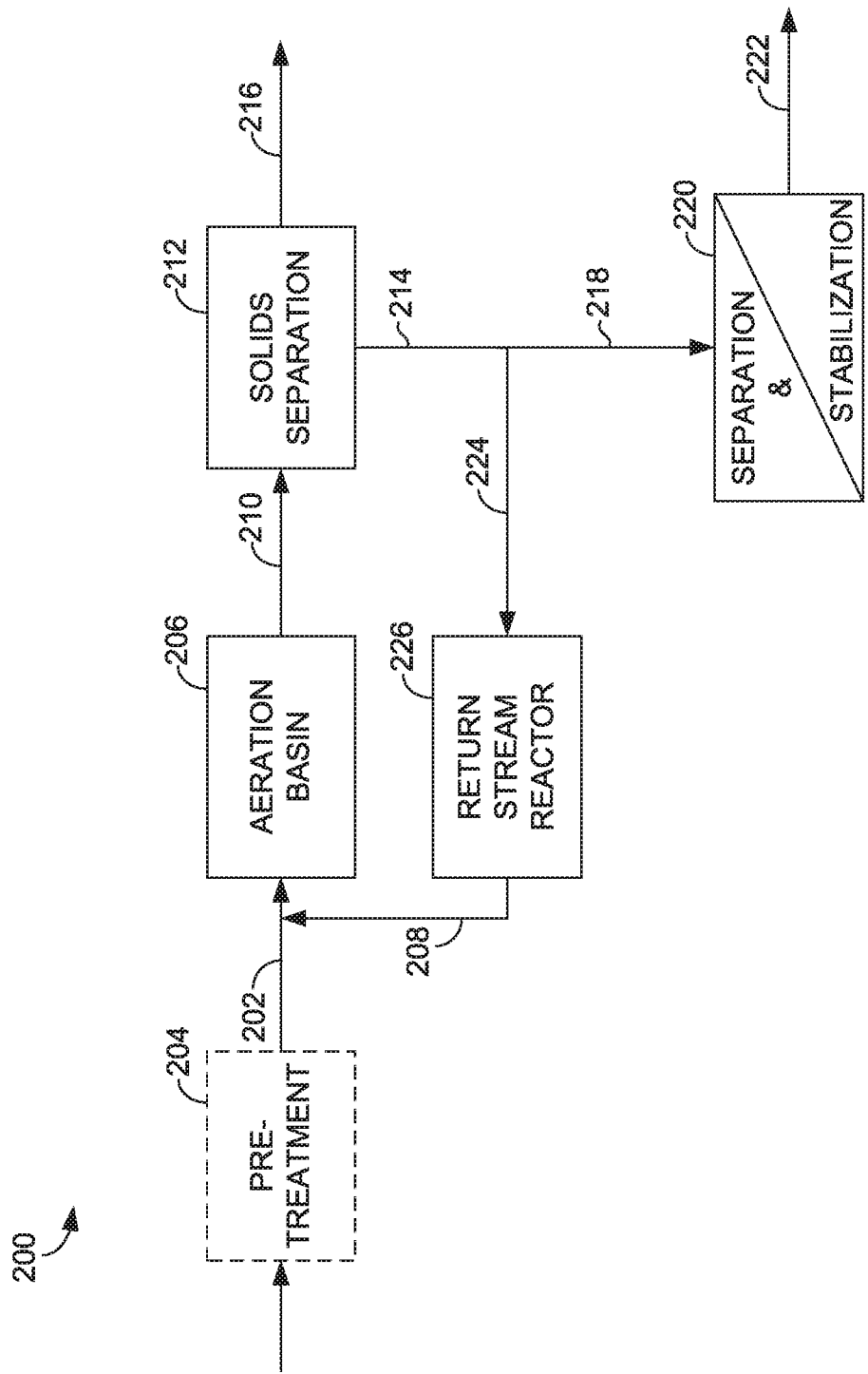
FIG. 2 illustrates a schematic diagram of PHA production during waste stream reclamation/organic resource recovery using a return stream reactor in accordance with another embodiment of the present invention.

While FIG. 1 illustrates an embodiment employing a single reactor (i.e., aeration basin 106), further embodiments may employ a return stream reactor in addition to a main stream reactor to provide the famine stage and feast stage separately that promotes PHA production. Turning now to FIG. 2, a schematic diagram is provided showing an embodiment of a process 200 employing a return stream reactor 226 in addition to an existing aeration basin 206. In some embodiments, an existing wastewater treatment process may be identified with an existing aeration basin (e.g., aeration basin 206), and the wastewater treatment process may be modified by adding a return stream reactor (e.g., return stream reactor 226) to provide a process (i.e., famine stage) that optimizes PHA production.

In accordance with the embodiment shown in FIG. 2, an influent waste stream 202 is provided that has constituent characteristics as described hereinabove. In some embodiments, this may optionally include a pre-treatment process 204, such as fermentation of solids and/or solids separation. The influent waste stream 202 and a RAS 208 are introduced into an aeration basin 206. In some embodiments, the operational parameters of the aeration basin 206 may include an HRT may be slightly higher than or equal to a conventional AS process, whereas the F/M ratio may be higher than or equal to a conventional AS process. In some particular embodiments, the operational parameters may include an HRT of approximately 8 hours to 2 days and an F/M ratio of 0.5 to 2.

A treated waste stream 210 from the aeration basin 206 is processed in a solids separation basin 212, such as a clarifier, to separate AS 214 from an effluent waste stream 216. A first portion of the AS 224 is introduced into a return stream reactor 226. In some embodiments, the return stream reactor 226 may be operated under an HRT of approximately 1 to 3 days and an F/M ratio of approximately 0.1 to 0.4.

A second portion of the activated sludge 218 is provided as a PHA-laden biomass to a separation and stabilization process 220. Similar to that discussed above with reference to FIG. 1, the separation and stabilization process 220 prevents microbes from consuming PHA as an internal carbon source following harvest and thereby produces a stabilized PHA-laden biomass 222. In some embodiments, the separation and stabilization process 220 may include dewatering (e.g., centrifugation) following by microbial stabilization (e.g., disinfection) and an ensuing drying process.

Figure 3:
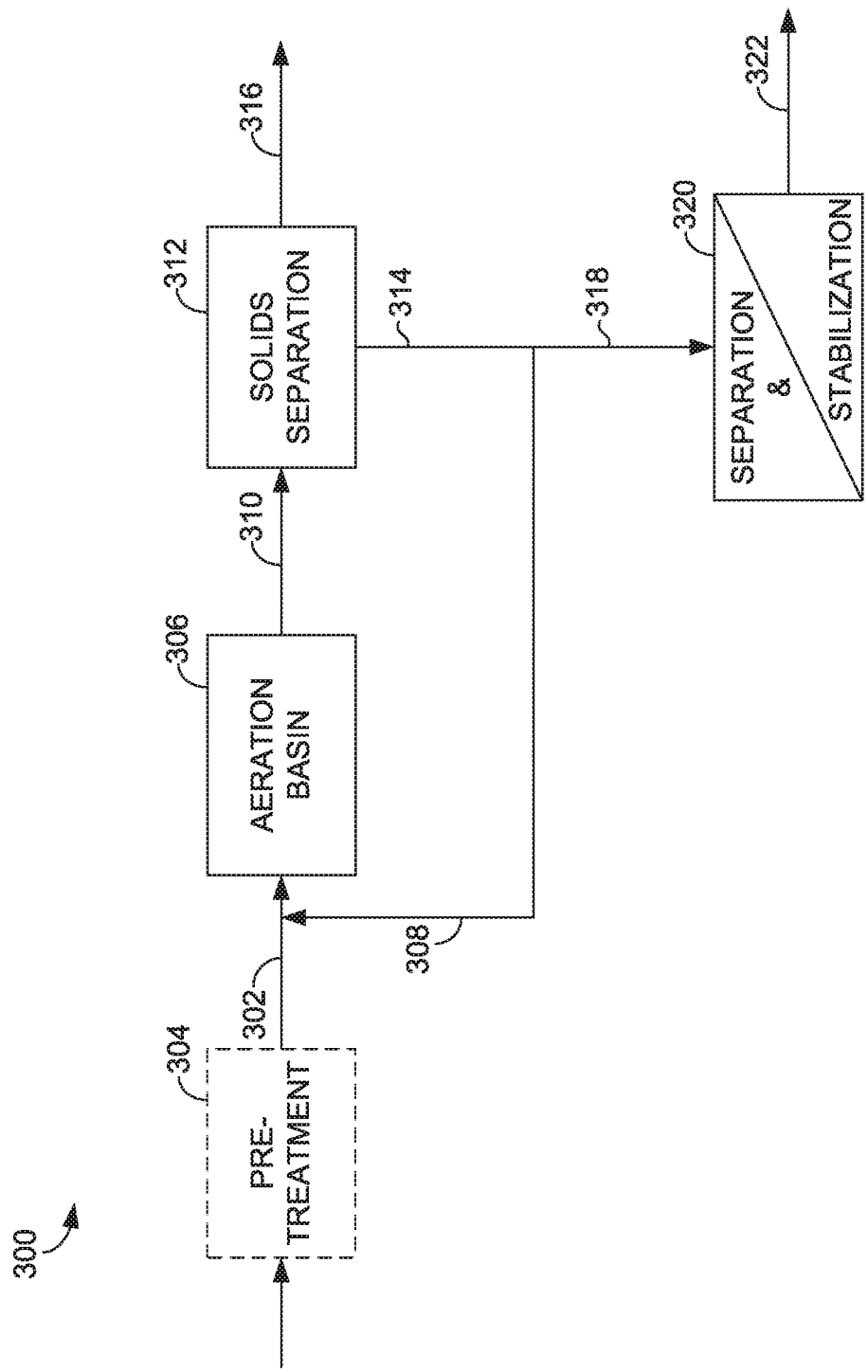
FIG. 3 illustrates a schematic diagram of PHA production during waste stream reclamation/organic resource recovery in accordance with a further embodiment of the present invention.

FIG. 3 provides a further embodiment for providing PHA production. The process 300 shown in FIG. 3 is similar to the process 200 of FIG. 2. The main distinction is that the return pipe returning the RAS 308 in the process 300 primarily provides the famine stage in place of the return stream reactor 226 in the process 200. In accordance with the embodiment shown in FIG. 3, an influent waste stream 302 is provided that has constituent characteristics as described hereinabove. In some embodiments, this may optionally include a pre-treatment process 304, such as fermentation of solids and/or solids separation. The influent waste stream 302 and a RAS 308 are introduced into an aeration basin 306. In some embodiments, the operational parameters of the aeration basin 306 may include an HRT that may be slightly higher than or equal to a conventional AS process, whereas the F/M ratio may be higher than or equal to a conventional AS process. In some particular embodiments, the operational parameters may include an HRT of approximately 8 hours to 2 days and an F/M ratio of 0.5 to 2.

A treated waste stream 310 from the aeration basin 306 is processed in a solids separation basin 312, such as a clarifier, to separate AS 314 from an effluent waste stream 316. A first portion of the activated sludge is returned to the aeration basin 306 as RAS 308 via a return pipe. The return pipe is aerated and operated under conditions similar to those discussed above for the return stream reactor 226 in the process 200. For instance, in some embodiments, the return pipe for the RAS 308 may be operated under an HRT of approximately 1 day and an F/M ratio of approximately 0.1 to 0.4. In this way, the return pipe with the RAS 308 provides a famine stage. In some embodiments, the HRT in the return pipe may be lower as the solids separations basin 312 may provide a famine environment, thereby contributing partially to the famine stage.

A second portion of the activated sludge 318 is provided as a PHA-laden biomass to a separation and stabilization process 320. The separation and stabilization process 320 prevents microbes from consuming PHA as an internal carbon source following harvest and thereby produces a stabilized PHA-laden biomass 322. In some embodiments, the separation and stabilization process 320 may include dewatering (e.g., centrifugation) following by microbial stabilization (e.g., disinfection) and an ensuing drying process.

It should be understood by one skilled in the art that although FIGS. 1-3 illustrate separate basins being employed, in some configuration, the basins can be provided with shared walls. For instance, the aeration basin 106 and solids separation basin 112 in FIG. 1 could be provided with a shared wall. Similarly, the aeration basin 306 and solids separation basin 312 in FIG. 3 could be provided with a shared wall. Such configurations would in essence provide a carousel operation with a cost-saving footprint. In addition, the return stream reactor 226 in FIG. 2 can be provided as a pipeline configuration employed with aeration to accommodate a famine stage.

Figure 4:
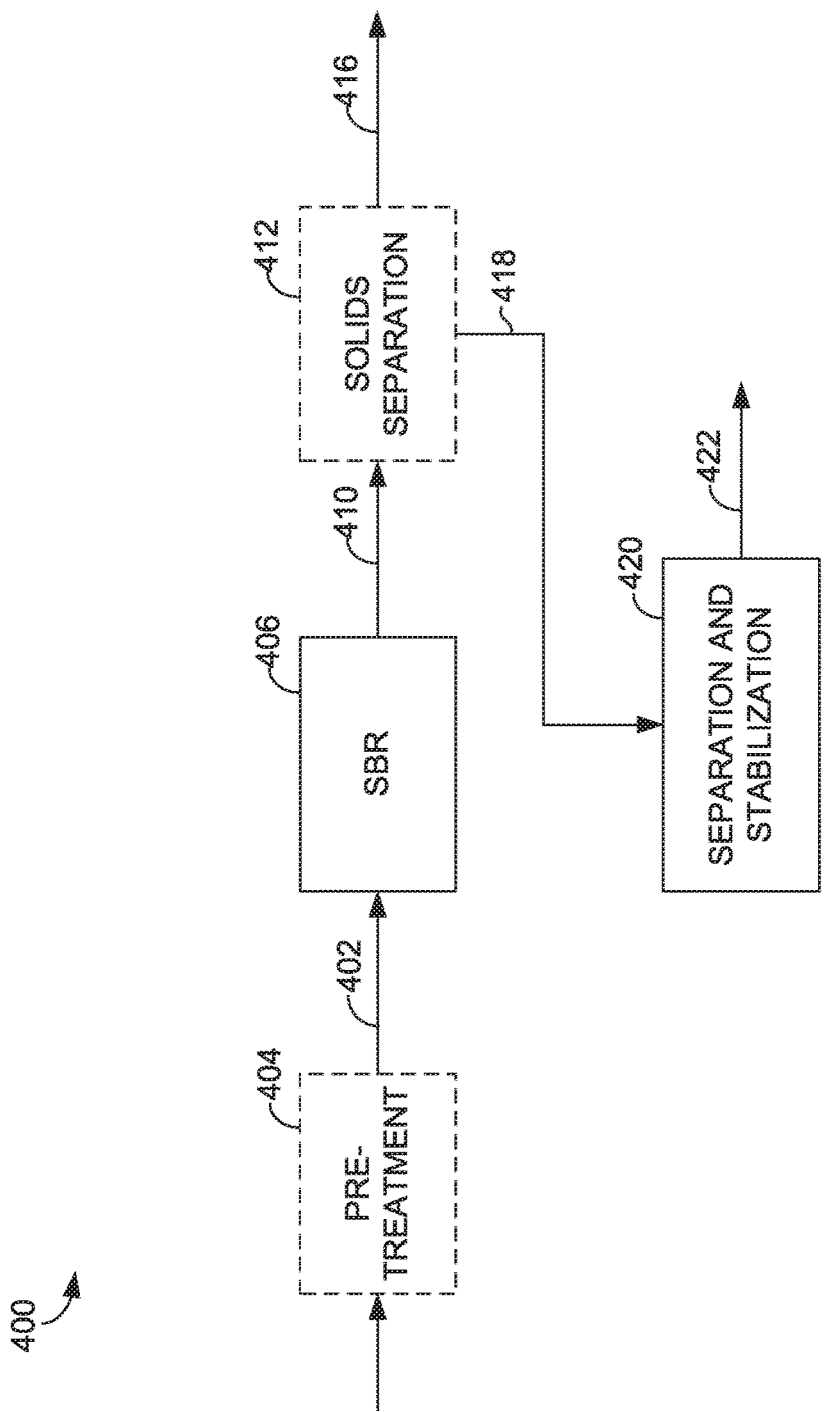
FIG. 4 illustrates a schematic diagram of PHA production during waste stream reclamation/organic resource recovery using a sequencing batch reactor (SBR) in accordance with another embodiment of the present invention.

While FIGS. 1-3 illustrate embodiments employing physically distinct famine and feast stage locations, further embodiments may employ a sequencing batch reactor (SBR) to provide a common physical location for providing the famine stage and feast stage that promotes PHA production. Turning now to FIG. 4, a schematic diagram is provided showing an embodiment of a process 400 employing a SBR 406 and a separation and stabilization process 420.

In accordance with the embodiment shown in FIG. 4, an influent waste stream 402 is provided that has constituent characteristics as described hereinabove. In some embodiments, this may optionally include a pre-treatment process 404, such as fermentation of solids and/or solids separation. The influent waste stream 402 is introduced into an SBR 406 and may be introduced to a separation and stabilization process 420.

In embodiments, the SBR 406 utilizes temporal sequences to provide a famine-feast regime in a single reactor. Instead of using one space for a famine stage and another space for a feast stage as in the embodiments illustrated in FIGS. 1-3, the SBR 406 is a single space for co-locating a famine-feast cycle. In embodiments, the cycle comprises the following steps: a first react step (famine), wherein the SBR 406 is operated under conditions in which PHA accumulating microorganisms consume PHA as an internal carbon source for survival during the famine state in order to enrich/select microorganisms capable of accumulating PHA; a fill step, wherein an influent waste stream 402 is introduced to the SBR 406; a second react step (feast), wherein the microorganisms capable of accumulating PHA consume the influent waste stream 402 by consuming available external substrate and converting it into intracellular PHA; a settle step; a drain step, wherein, with or without the use of an optional solids separation process 412, effluent is discharged and excess/a portion of PHA-laden biomass 418 is introduced to the separation and stabilization process 420; and an optional idle step. In aspects, the excess PHA-laden biomass 418 may be a portion of PHA accumulating microorganisms existing at the end of the cycle, with the remainder being retained in the SBR for one or more subsequent cycles.

The sequence provided in accordance with embodiments described herein differs from conventional SBR operation. Conventional SBR operations typically include 4 steps: Fill, React, Settle, Drain (and optionally an Idle step). This is in contrast to embodiments described herein that include two React steps with a Fill step in between the React steps in order to provide a famine-feast regime to select and enrich microorganisms capable of producing PHA. The React step prior to the Fill step provides a famine stage, while the React step after the Fill step provides a subsequent feast stage.

In some embodiments, a treated waste stream 410 from the SBR 406 is processed in an optional solids separation basin 412, such as a clarifier, to separate excess PHA-laden biomass 418 from an effluent waste stream 416. The PHA-laden biomass 418 is introduced to a separation and stabilization process 420. In other embodiments, a treated waste stream 410 from the SBR 406 produces an effluent waste stream 416 and an excess PHA-laden biomass 418, the latter being introduced to the separation and stabilization process 420. In both embodiments, and similar to that discussed above with reference to FIG. 1, the separation and stabilization process 420 prevents microorganisms from consuming PHA as an internal carbon source following harvest and thereby produces a stabilized PHA-laden biomass 422. In some embodiments, the separation and stabilization process 420 may include dewatering (e.g., centrifugation) followed by microbial stabilization (e.g., disinfection) and an ensuing drying process.

EXAMPLE

Embodiments of the present invention will now be further illustrated by the following, non-limiting examples.

Example 1

An industrial waste stream (e.g., high-strength COD) was found to be with COD of 2,500 mg/L, SCFAs of 1.2 mM, polysaccharides of 0.8 mM, protein of 0.4 mM, and TSS of 500 mg/L. As this waste stream met the constituents criteria with the exception of TSS, solid separation was employed as a pre-treatment process to reduce solids to a desirable level of TSS less than 200 mg/L in a pre-treated waste stream. The pre-treated waste stream was then introduced at a location approximately one-third along the length of an aeration basin. The aeration basin was operated under a HRT of 3 days and F/M ratio of 1.5. RAS was introduced at the beginning of the aeration basin. In this manner, the aeration basin provided a famine-feast regime that enriched/selected microorganisms capable of accumulating PHA. A treated waste stream exiting the aeration basin was processed in a clarifier to separate AS from an effluent. A first portion of the AS was returned to the aeration basin (as noted above). A second portion of the AS was treated using centrifugation followed by disinfection and an ensuing drying process to provide a stabilized PHA-laden biomass. Meanwhile, the effluent was ready to discharge.

Example 2

As a prophetic example of an embodiment employing a return stream reactor in addition to an aeration basin, a municipal wastewater treatment plant wastewater (e.g., low-strength COD waste stream) with COD of 250 mg/L, SCFAs of 0.2 mM, polysaccharides of 0.3 mM, protein of 0.2 mM, and TSS of 80 mg/L after existing primary sedimentation is processed. As this waste stream is not in a preferred range of COD and SCFAs concentration, a fermentation pre-treatment process is employed as a pre-treatment (e.g., fermentation of solids captured in a primary sedimentation step) to increase COD and SCFAs to a desirable level of COD loading more than 800 mg/L/d and SCFAs concentration more than 1 mM to provide constituent characteristics. In addition, solids collected from the primary sedimentation are introduced into the fermentor to increase COD and SCFAs concentration in the influent waste stream. The influent waste stream and a RAS are introduced into an aeration basin. The aeration basin is operated under HRT of approximately 1 day and F/M ratio of 0.8. A treated waste stream from the aeration basin is processed in a clarifier to separate AS from an effluent. A first portion of the AS is introduced into a return stream reactor. The return stream reactor is operated under HRT of 2.5 days and the F/M ratio of approximately 0.2. A second portion of the AS is separated by centrifugation followed by disinfection and an ensuing drying process to provide a stabilized PHA-laden biomass. Meanwhile, the effluent is ready to discharge.

Example 3

As a prophetic example of an embodiment employing a SBR, an industrial waste stream (e.g., high-strength COD) is found to be with COD of 2,500 mg/L, SCFAs of 1.2 mM, polysaccharides of 0.8 mM, protein of 0.4 mM, and TSS of 100 mg/L is processed. As this waste stream meets the constituent criteria, the waste stream is introduced to the SBR. The SBR is operated under a HRT of 3 days and F/M ratio of 1.5. The SBR is operated with a first react step (i.e., famine) followed by fill and second react steps (i.e., feast) to provide a famine-feast regime to select and enrich microorganisms capable of accumulating PHA. After settling, a portion of the PHA-accumulating microorganisms (i.e., excess PHA-laden biomass) are drained and treated using centrifugation followed by disinfection and an ensuing drying process to provide a stabilized PHA-laden biomass. Meanwhile, the effluent is ready to discharge.

The present invention has been described in relation to particular embodiments, which are intended in all respects to be illustrative rather than restrictive. Alternative embodiments will become apparent to those of ordinary skill in the art to which the present invention pertains without departing from its scope.

From the foregoing, it will be seen that this invention is one well adapted to attain all the ends and objects set forth above, together with other advantages which are obvious and inherent to the system and method. It will be understood that certain features and subcombinations are of utility and may be employed without reference to other features and subcombinations. This is contemplated by and is within the scope of the claims.

What is claimed is:

1. A process for polyhydroxyalkanoate (PHA) production during wastewater treatment, the process comprising:
operating a sequencing batch reactor (SBR) under a first react step that provides a famine stage that selects and enriches microorganisms capable of accumulating PHA, wherein the SBR comprises a single space for co-locating the first react step and a second react step;
introducing a waste stream into the SBR subsequent to operating the SBR under the first react step;
after introducing the waste stream into the SBR, operating the SBR under the second react step that provides a feast stage that promotes the production of intracellular PHA by the microorganisms in the SBR;
removing a PHA-laden biomass from the SBR subsequent to operating the SBR under the second react step; and
processing the PHA-laden biomass to produce a stabilized PHA-laden biomass.

2. The process of claim 1, wherein the process further comprises providing the waste stream by:
evaluating characteristics of the waste stream; and
determining that the waste stream is suitable for increased PHA production based on the characteristics of the waste stream.

3. The process of claim 2, where the characteristics of the waste stream evaluated comprise a short chain fatty acids concentration, a polysaccharides concentration, a protein concentration, and a total suspended solids concentration.

4. The process of claim 1, wherein the process further comprises pre-treating an initial waste stream to produce the waste stream suitable for increased PHA production.

5. The process of claim 4, wherein pre-treating the initial waste stream comprises processing the initial waste stream using solids fermentation.

6. The process of claim 4, wherein pre-treating the initial waste stream comprises reducing total suspended solids.

7. The process of claim 1, further comprising an idle cycle.

8. The process of claim 1, wherein the waste stream has short chain fatty acids more than 1 mM.

9. The process of claim 1, wherein the waste stream has polysaccharides less than 6 mM.

10. The process of claim 1, wherein the waste stream has protein less than 1 mM.

11. The process of claim 1, wherein the waste stream has total suspended solids concentration less than 200 mg/L.

12. The process of claim 1, wherein processing the PHA-laden biomass to produce the stabilized PHA-laden biomass comprises processing an excess portion of the PHA-laden biomass using dewatering, microbial inactivation, and drying.

13. A process for polyhydroxyalkanoate (PHA) production during wastewater treatment, the process comprising:
operating a reactor, comprising a single space for co-locating a famine-feast cycle, under operational parameters providing a famine stage of the famine-feast cycle to select microorganisms capable of accumulating PHA;
subsequent to the famine stage, introducing a waste stream to the selected microorganisms capable of accumulating PHA in the reactor under operational parameters to provide a feast stage of the famine-feast cycle that promotes production of intracellular PHA by the microorganisms in the reactor;
removing a PHA-laden biomass from the reactor subsequent to the feast stage; and
processing the PHA-laden biomass to produce a stabilized PHA-laden biomass.

14. The process of claim 13, wherein the reactor comprises an aeration basin.

15. The process of claim 14, wherein the famine stage is provided in a first location within the single space of the aeration basin and the feast stage is provided in a second location within the single space of the aeration basin.

16. The process of claim 13, wherein the reactor comprises a sequencing batch reactor, and wherein the famine stage comprises a first react step and the feast stage comprises a second react step.

17. A process for polyhydroxyalkanoate (PHA) production during wastewater treatment, the process comprising:
identifying a biodegradable, high-carbon content waste stream having PHA precursor metabolites, the waste stream having a short chain fatty acids more than 1 mM, polysaccharides less than 6 mM, proteins less than 1 mM, and a total suspended solids concentration less than 200 mg/L;
operating a sequencing batch reactor (SBR), comprising a single space for co-locating a famine-feast cycle, under operational parameters that provide a famine sequence of the famine-feast cycle to enrich and select microorganisms capable of accumulating PHA;
subsequent to operating the SBR to provide the famine sequence, introducing the waste stream into the SBR under operational parameters that provide a feast sequence of the famine-feast cycle that promotes the production of intracellular PHA by the microorganisms in the SBR;
obtaining a PHA-laden biomass from effluent from the SBR subsequent to the feast sequence; and
processing the PHA-laden biomass to produce a stabilized PHA-laden biomass.

18. The process of claim 17, wherein the processing the PHA-laden biomass to produce the stabilized PHA-laden biomass prevents the microorganisms from consuming PHA as an internal carbon source, and wherein the processing comprises dewatering followed by microbial stabilization to provide the stabilized PHA-laden biomass.

19. The process of claim 17, wherein the PHA-laden biomass is obtained via draining and further treated by dewatering followed by disinfection and an ensuing drying process to provide the stabilized PHA-laden biomass.

20. The process of claim 17, further comprising retaining a remainder of the PHA-laden biomass in the SBR for at least one additional famine-feast cycle.

* * * * *